United States Patent [19]

Elias

[11] Patent Number: 5,107,531
[45] Date of Patent: Apr. 21, 1992

[54] APPARATUS AND METHOD FOR IMPROVING DIAGNOSTIC X-RAYS

[76] Inventor: Robert J. Elias, 6613 Dublin Loop W., Apt. #3, Colorado Springs, Colo. 80918

[21] Appl. No.: 544,713

[22] Filed: Jun. 27, 1990

[51] Int. Cl.⁵ .............................................. G03B 42/02
[52] U.S. Cl. ................................... 378/175; 378/167; 378/205
[58] Field of Search ............... 378/175, 174, 181, 167, 378/205, 163

[56] References Cited

U.S. PATENT DOCUMENTS

| | | | |
|---|---|---|---|
| 1,219,965 | 3/1917 | Leisenring. | |
| 2,063,878 | 12/1936 | Linke et al. | 378/175 |
| 2,111,903 | 3/1938 | Rona | 378/181 |
| 2,545,899 | 3/1951 | Soba | 250/66 |
| 3,959,656 | 5/1976 | Peters | 250/476 |
| 3,976,887 | 8/1976 | Holzermer et al. | 250/468 |

Primary Examiner—Janice A. Howell
Assistant Examiner—Don Wong
Attorney, Agent, or Firm—Stanton E. Collier; Donald J. Singer

[57] ABSTRACT

The present invention is especially suited for tomographic X-ray studies wherein dozens of exposures are required. A film cassette spacer having selected dimensions and having selected markings thereon is placed adjacent to the film cassette on a mechanically centering bucky tray in an X-ray machine. By use of the collimating means in the X-ray head, the number of exposures on the film can be maximized but still maintaining quality exposures for reading.

11 Claims, 3 Drawing Sheets

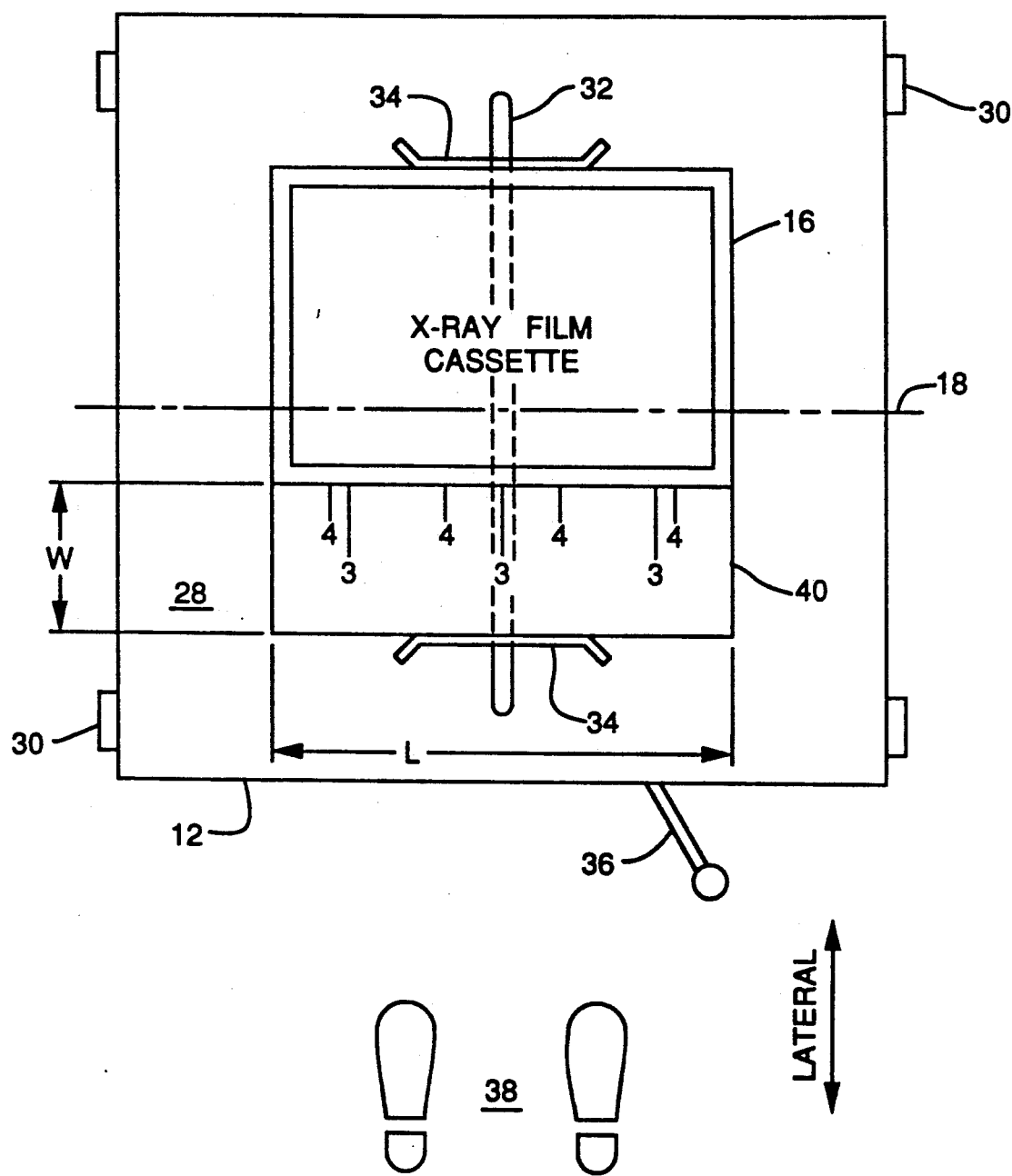

APPARATUS AND METHOD FOR IMPROVING DIAGNOSTIC X-RAYS

STATEMENT OF GOVERNMENT INTEREST

The invention described herein may be manufactured and used by or for the Government for governmental purposes without the payment of any royalty thereon.

BACKGROUND OF THE INVENTION

The present invention relates to x-ray machines, and, in particular, to x-ray machines having film trays that mechanically center the film cassette laterally upon the x-ray table.

It is well known that many x-ray machines have examination tables with film cassette (bucky) trays therein that mechanically center the film cassettes of varying sizes on a longitudinal center line of the table. The bucky tray can move longitudinally on the table, but not laterally except for the purpose of inserting and removing film cassettes. Another feature is a collimating means located in the x-ray head. By use of the collimating means, the area of exposure may be adjusted to minimize unnecessary exposure to the patient where a reticle is projected onto the table. The size of the projected reticle is controlled by a diaphragm therein. The x-ray source is typically positioned on the longitudinal center line of the x-ray table.

If one desired to take multiple exposures on one sheet of film, each exposure was always centered on the film because of the bucky tray centering device. Depending upon the film size and the collimated area, 2 or 3 exposures could be placed on One sheet of film. It is clear from this standard practice that a significant amount of film area was wasted.

Prior devices, for example, to maximize film usage are as follows: U.S. Pat. No. 1,219,965 discloses a partially enclosed tray having a rectangular opening therein. The film is moved within the tray to expose selected areas. This device has a fixed opening size therein. The opening is fixed within the tray and limited to a certain film size. U.S. Pat. No. 2,545,899 discloses a partially enclosed film tray having movable openings to produce multiple exposures. The size of the openings are fixed as well as the distance from the center thus only a particular film size would produce optimum results. U.S. Pat. No. 3,955,656 discloses a film tray moveable under an aperture on an x-ray table. The tray is marked for a fixed size of film cassette and is able to produce multiple exposures by adjusting the cassette in the tray according to the guide lines thereon. These patents fail to address the problem of the present invention wherein film cassettes of various sizes are used in a buck tray having a fixed mechanically centering device therein.

The need exists for an apparatus and method for being able to take multiple exposures of a size to be determined by the medical procedure and to optimize this size to the size of the film being used in a mechanically operated x-ray machine.

SUMMARY OF THE INVENTION

The present invention is directed at an apparatus and method to optimize film usage in an x-ray machine.

An x-ray machine having a bucky tray, i.e., one where a single film cassette is mechanically centered, may use film cassettes of various sizes; the invention uses cassette spacers corresponding to various film cassette sizes which are placed into the bucky tray next to the film cassette and aligned therewith in the centering device. As a result thereof, the film cassette is shifted a predetermined distance away from the center line of the x-ray table. A plurality of markings on the cassette spacers allows one to position the exposures on the film accurately without the use of masks such as illustrated in U.S. Pat. Nos. 2,545,899 and 3,050,656, for example. The use of the invention's masks would be applicable to x-ray machines without optical collimating means therein which projects a lit area onto the x-ray table. The film cassette and cassette spacers are moved for each exposure. After the required number of exposures are taken in one column, the cassette spacer is moved to the other side of the film cassette so as to shift the cassette. The next column of exposures are taken resulting in two columns of exposures rather than one which resulted from past techniques. If a collimator is not available on the x-ray head to localize and minimize the exposure, masks can be placed on the film cassette.

It is therefore one object of the present invention to maximize the number of appropriate exposures on the film of any given size.

Another object of the present invention is to provide an apparatus and method that saves film, reduces developing chemicals, reduces exam time, and reduces the time needed to examine the film.

Another object of the present invention is to provide an apparatus and method for minimizing radiation exposure and improving the x-ray quality.

Another object of the present invention is to provide an apparatus and method for use in tomographic studies.

These and many other objects and advantages of the present invention will be readily apparent to one skilled in the pertinent art from the following detailed description of the invention and the related drawings.

BRIEF DESCRIPTION OF THE DRAWINGS

FIG. 1 illustrates by top view the film cassette spacer adjacent to the x-ray film cassette in the bucky tray.

DESCRIPTION OF THE PREFERRED EMBODIMENTS

Figure 3:
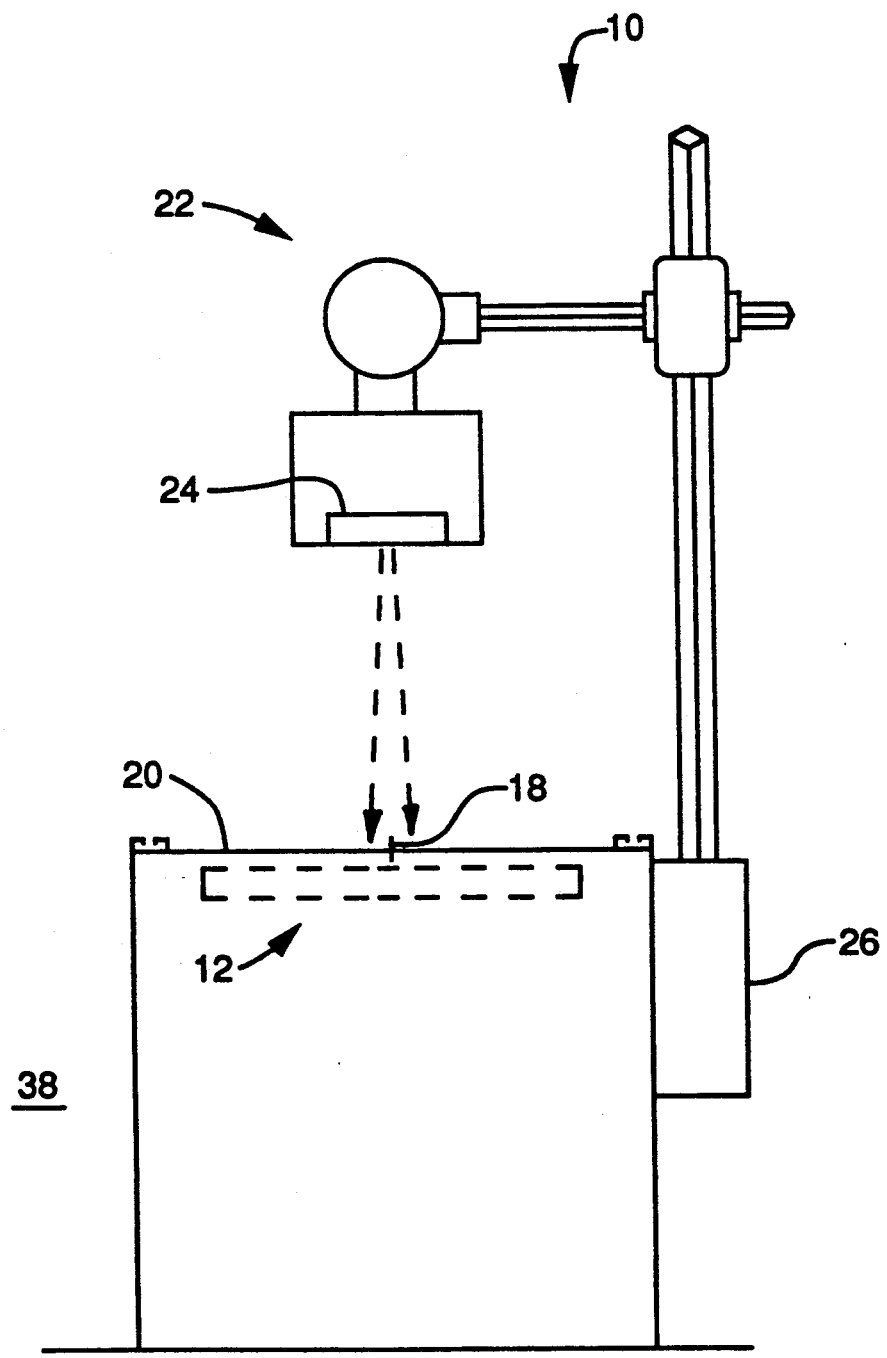
FIG. 3 illustrates by end view an x-ray machine.

Referring to FIG. 3, a conventional x-ray machine 10 is shown. This machine 10 may be a General Electric model, Siemens model, etc., having a mechanically operated cassette (bucky) tray 12 which normally centers a film cassette 16, FIG. 1, on a center line 18 of an x-ray table 20. An x-ray head 22 houses the source of x-rays, not shown, and, preferably, a collimating means 24 which can be used to adjust the exposure size. Typically, the collimating means 24 includes a light source for projecting a reticle structure onto the table 20. Machine 10 may further include a drive means 26 for moving head 22 in an arcuate path for taking tomographic pictures, for example. It is understood that tomographic x-ray pictures are those that picture details at a particular area at a multitude of layers for determining the injury, for example, or defect. Because of this procedure, many pictures are required by the examining radiologist to study the problem in question.

The time required to take these pictures by the radiologic technician can be extensive. The patient, as a result, may move and cause pictures to be blurry or marginal thus making the diagnosis more difficult resulting in additional pictures and exposure to x-rays. One would desire a technique to minimize the time required and still obtain quality x-ray pictures. Other benefits resulting from this invention will be evident.

Referring to FIG. 1, the bucky tray 12 is shown in a top view as seen without the x-ray table top thereon. The bucky tray 12 has a platform 28 with appropriate wheels 30 thereon which travel on tracks, not shown, in the table 20. In the platform 28 is a lateral slot 32 having projecting above the platform 28 a pair of movable clamps 34 that move in unison to or away from the center line 18 by action of a lever 36; the mechanical means connecting the lever 36 to the clamps 34 is not shown but considered conventional.

The view of bucky tray 12 is that shown when the technician stands at a location 38, FIGS. 1 and 3 and looks down on the table 20, if the bucky tray 12 were visible from above.

An x-ray film cassette spacer 40 is shown abutted against the film cassette 16 on its left lateral side. The length, L, and the width, W, FIGS. 1 and 2A, of the spacer 40 is determined by the size of the film and the cassette size as herein detailed. In practice the film size ranges from $18 \times 24$ cm., $24 \times 24$ cm., $24 \times 30$ cm., and $30 \times 35$ cm. The corresponding sizes for the spacer 40 are $8.57 \times 26.67$ cm., $1.75 \times 26.67$ cm., $11.75 \times 33.02$ cm. and $13.65 \times 38.10$ cm. The spacer 40 is typically as long as film cassette the width is equal to one-half of the width of the film cassette. The length should be as close to the length of the film cassette 16 so that it can be quickly placed adjacent thereto and aligned thereon at the edges with the use of one's fingers.

In practice, the film cassette width should be less than about two-thirds the maximum opening between the clamps 34 and the spacer 40 width, W, is about one-half the film cassette width.

Figure 2A:
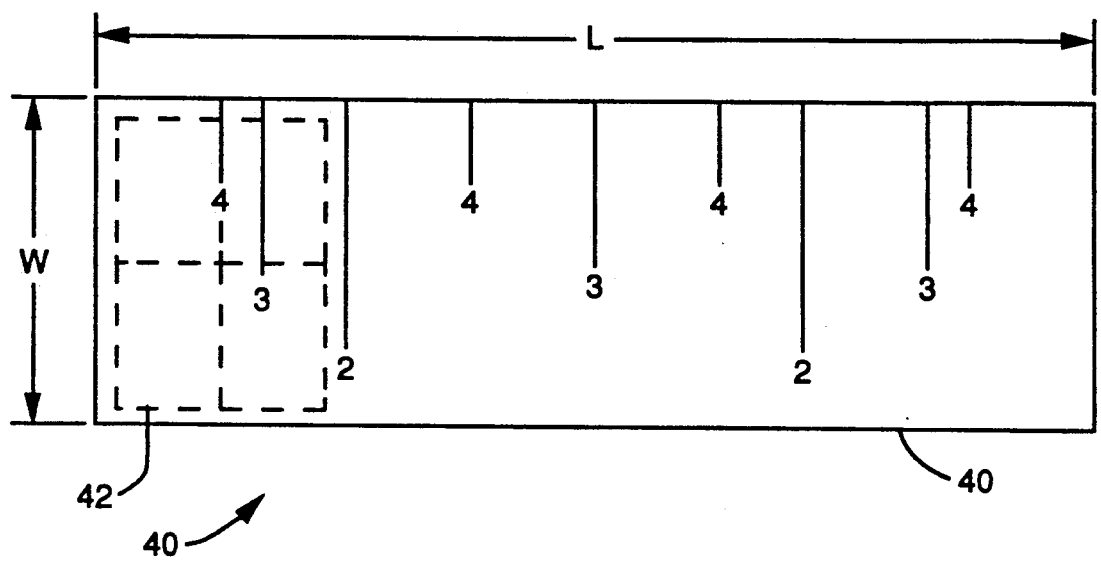
FIGS. 2A and 2B illustrate by top view several embodiments of the cassette spacer with guide markings thereon.

Referring to FIG. 2A, the spacer 40 is shown with guide marks on one side thereon. A guide line 4 indicates that there will be 4 pictures on a side with 8 total on each sheet of a size.

In order to insure that each picture falls in the proper area, the bucky tray 12 is pulled out of the table 20 so that the spacer 40 is visible thereon. The x-ray head 22 is moved near to the operator's position and a collimating reticle 42, shown in outline in FIG. 2A is adjusted so that the reticle 42, for example, occupies one-quarter of the spacer 40 and is centered on the first guide line 4 by moving the combination of the spacer 40 and the film cassette 12 horizontally. The bucky tray 12 is pushed into the x-ray table 20. Before this occurs the patient's body part is placed under the x-ray head 22. The size of the area to be exposed is determined by the technician which dictates how many pictures can be put on one sheet, if possible. After the exposure, the bucky tray 12 is pulled out and the spacer 40 and film cassette 16 are shift to the left, for example, till the next guide line 4 is centered on slot 32 or the center line running laterally in the bucky tray 12. This process is repeated 2 more times, for example. After this the spacer 40 is placed on the other lateral side of the film cassette 16 and the lever 36 is closed to center the combination as noted above. The first guide line 4 is then aligned with the slot 32, the exposure taken, and then the combination is shifted to the left and the above repeated until all 4 pictures are taken on this side. At this point there are 8 exposures on the sheet.

Figure 2B:
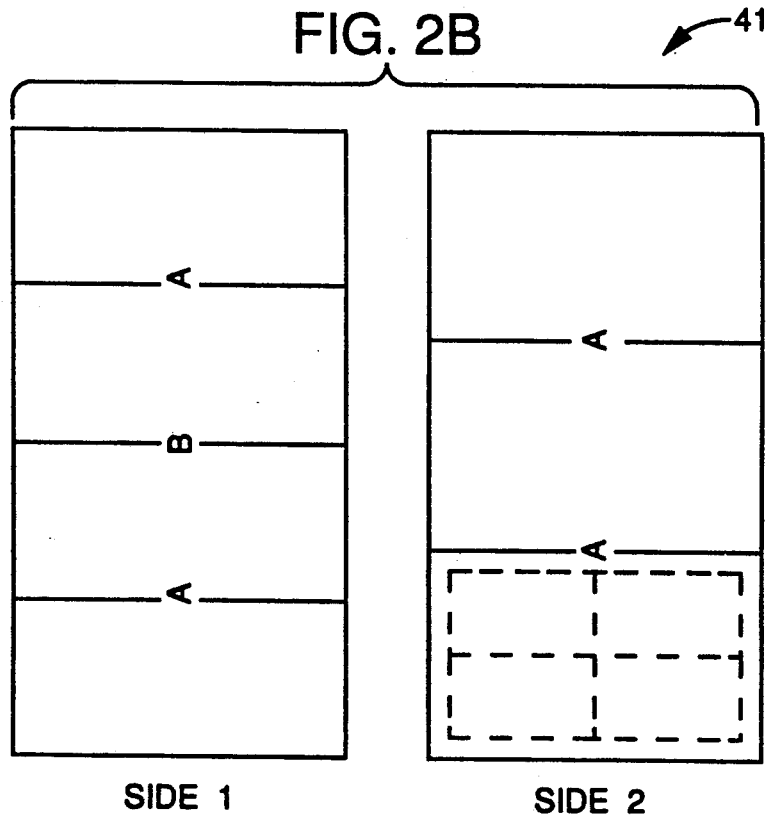

Referring to FIG. 2B, another embodiment of the spacer 41 is shown having guide line markings on opposite sides to reduce confusion.

These markings are used to allow the x-ray technician to accurately collimate and center the x-ray beam to the proper area on the film. The markings may be of different colors in order to avoid confusion when doing exams. The lines may be made of permanent ink or paint put into etches in the spacer. Line A on side one of the spacer 41 would be a different color than line B. These lines are used to allow the technician to select the number of exposures desired. On side 1, the technician would initially center the reticle on the line A to place four exposures on one sheet. The reticle would be centered on line B to place two exposures on one sheet. On side 2 the reticle would be centered in the open area for placing six exposures on one sheet of film. Alternately on side 2, there could be three lines A and the reticle could be centered on these. The sides would be marked to indicate the number of exposures per sheet: 2 on one, 4 on one, 6 on one and 8 on one as appropriate. The number of lines on each spacer will depend on the number of exposures possible for that film size.

It is seen from the above that there are several variables in this process to minimize film use. A skilled radiologic technician should be able to determine the area to be x-rayed, the number of exposures, and the size of film.

The spacers 40 can be made from a stock $2 \times 4 \times \frac{1}{4}$ sheet of polyethylene, for example. The guide lines can be scribed thereon and appropriately colored and/or numbered.

If the x-ray machine 10 does not have a high quality collimating means, lead masks covering one-half side of the film cassette and in contact thereon can be used. Additional masks having a quarter corner removed from a mask that covers the whole film cassette can be used to place four exposures on a sheet. These would be used in combination with the spacer 40 to center the exposure on the appropriate area.

This apparatus and method significantly reduce the cost of x-ray films in such procedures as in tomography studies. This results in fewer films without any loss in details or quality, saves films, film storage space, exam time and helps the radiologist study the films.

With the GE x-ray machine, more than two exposures can be placed on $18 \times 24$ cm., $24 \times 24$ cm., and $24 \times 30$ cm. film. On the $30 \times 35$ cm. film, the spacer does not re-center the film so only two exposures can be made thereon.

Examples of film and money savings when using the film spacers for tomographic studies are herein noted:

Ankle Tomogram AP and Lat Tomos: $24 \times 30$ cm. film is used. Without the spacer 2 exposures were put on one film. Required 24 films costing $16.32. With the spacer 4 exposures were put on one film. Required 12 films costing $8.16. Savings are $8.16 per exam.

TMJ Tomograph open and closed Laterals, both sides: $18 \times 24$ cm. film used. Without the spacer, put 2 to 3 exposures on one film. Required 36 exposures using 12 films costing $5.04. With the spacer, 9 exposures were put on one film. Used 4 films costing $1.68. Savings are $3.36 per exam.

Lumbar Spine Tomograms Ap and Laterals: $24 \times 30$ cm. film used. Without the spacer, one exposure per film. Required 30 exposures costing $20.40. With the spacer, two exposures per film. Required 15 films costing $10.20. Savings are $14.55 per exam. Using 30×35 cm. film, the savings per exam are $14.55.

Generalized savings on multiple exams:

10 Ankle tomos on 24×30 cm. film saved $81.60;

10 TMJ tomos on 18×24 cm. film saved $33.60;

10 Lumbar tomos on 24×30 cm. film saved $102.00; and

10 Lumbar tomos on 30×35 cm. film saved $145.00.

These savings do not reflect the time in manhours or the savings in chemicals used to develop the additional film as well as the wear and tear on the processors and x-ray tubes.

Clearly, many modifications and variations of the present invention ar possible in light of the above teaching and it is therefore understood that within the inventive scope of the inventive concept, the invention may be practiced otherwise than specifically claimed.

What is claimed is:

1. An apparatus for producing a plurality of x-ray exposures upon a film in a film cassette held within a mechanically centering bucky tray, the mechanically centering bucky tray mounted in an x-ray machine having an optical collimating means therein for defining an exposure area, said apparatus comprising:
   a film cassette spacer, said film cassette spacer being positioned on a lateral side of the film cassette to be exposed on the mechanically centering bucky tray, said film cassette spacer having a length substantially equal to a longitudinal length of the film cassette and a lateral width substantially equal to one-half a width of the film cassette, and
   means for guiding a positioning of the combination of the film cassette and said spacer in the bucky tray, said means for guiding being placed upon said spacer, said means for guiding provides the ability to closely place a plurality of exposures upon a side of an x-ray film in the film cassette.

2. An apparatus as defined in claim 1 wherein said means for guiding are placed upon opposite sides of said spacer.

3. An apparatus as defined in claim 1 wherein said means for guiding is rectangularly shaped body having two sides, said means for guiding are placed upon only one side of said spacer.

4. An apparatus as defined in claim 2 wherein said means for guiding comprises a plurality of guide lines for indicating the size of the exposure and the location of the exposure on the film, said guide lines being parallel to a lateral direction.

5. An apparatus as defined in claim 3 wherein said means for guiding comprises a plurality of guide lines for indicating the size of the exposure and the location of the exposure on the film.

6. An apparatus as defined in claim 1 wherein the maximum number of exposures on x-ray film is 2N wherein $1 \leq N \leq 4$ and N is an integer.

7. A method of producing a plurality of x-ray exposures upon a film in a film cassette, the film cassette held within a mechanically centering bucky tray, said method comprising the steps of:
   a. placing a selected body part upon an x-ray table;
   b. selecting a minimum necessary exposure size of said body part;
   c. selecting a film size to maximize the number of exposures of said exposure size;
   d. selecting an appropriate film cassette spacer for said film size;
   e. placing said film cassette and said spacer in said buck tray;
   f. centering a desired area of said exposure size by moving a combination of said film cassette and said spacer to a center position on the bucky tray;
   g. sliding inward the bucky tray into a picture taking position;
   h. exposing the desired area;
   i. sliding outward the bucky tray;
   j. moving the combination to a next desired area and repeating steps g to j until one-half of said film is exposed;
   k. moving the spacer to an opposite side of the film cassette;
   l. repeating steps f to j so that the film is exposed in all of the desired area;
   m. removing the film cassette and the spacer; and
   n. processing the film with the film cassette.

8. A method as defined in claim 7 wherein the steps are repeated to produce an appropriate tomographic study.

9. A method as defined in claim 7 wherein the spacer is marked with appropriate areas for use in centering a desired areas for multiple exposures on the film.

10. A method as defined in claim 7 further including an x-ray machine having a collimating means for projecting a reticle , the reticle being used to center the combination on the desired area.

11. A method as defined in claim 7 wherein, an x-ray machine without optical collimating means, a mask being one half the width of said film cassette and being about the same length of said cassette is placed upon said film cassette over the x-ray film not being exposed.

* * * * *